(12) United States Patent
Sullivan

(10) Patent No.: US 10,856,708 B2
(45) Date of Patent: Dec. 8, 2020

(54) PORTABLE TOILET

(71) Applicant: Efrat Sullivan, Rutherford, NJ (US)

(72) Inventor: Efrat Sullivan, Rutherford, NJ (US)

( * ) Notice: Subject to any disclaimer, the term of this patent is extended or adjusted under 35 U.S.C. 154(b) by 1 day.

(21) Appl. No.: 16/055,880

(22) Filed: Aug. 6, 2018

(65) Prior Publication Data

US 2019/0082899 A1 Mar. 21, 2019

Related U.S. Application Data

(60) Provisional application No. 62/559,018, filed on Sep. 15, 2017.

(51) Int. Cl.
*A47K 11/06* (2006.01)
*A61F 5/455* (2006.01)
*A47K 11/02* (2006.01)
*A61F 5/451* (2006.01)

(52) U.S. Cl.
CPC ............ *A47K 11/06* (2013.01); *A47K 11/026* (2013.01); *A61F 5/451* (2013.01); *A61F 5/4556* (2013.01)

(58) Field of Classification Search
CPC ..... A47K 11/06; A47K 11/026; A61F 5/4556; A61F 5/451
See application file for complete search history.

(56) References Cited

U.S. PATENT DOCUMENTS

| | | | |
|---|---|---|---|
| 2,404,384 A | 7/1946 | Curkjian | |
| 2,796,865 A | 6/1957 | Reinhardt | |
| 2,875,451 A | 3/1959 | Wilson | |
| 3,095,578 A | 7/1963 | Stanford | |
| 3,122,397 A * | 2/1964 | Mintz | A47C 9/10 297/188.13 |
| 3,329,973 A | 7/1967 | Bobbe | |
| 3,374,790 A * | 3/1968 | Mayhorne | A61F 5/4556 604/347 |
| 3,403,410 A * | 10/1968 | Benzel | A61F 5/44 4/144.2 |
| 3,432,865 A | 3/1969 | Schwartz | |
| 3,597,770 A | 8/1971 | Jacuzzi et al. | |
| 3,718,431 A | 2/1973 | Wild | |
| 5,243,712 A * | 9/1993 | Cross | A61F 5/4556 4/144.2 |
| 6,070,277 A * | 6/2000 | Thomas | A47K 11/02 4/484 |
| 6,813,786 B1 * | 11/2004 | Pier | A47K 11/02 4/484 |
| 6,851,131 B1 * | 2/2005 | Adams | A47K 13/14 4/245.1 |
| 7,073,212 B1 * | 7/2006 | Moffat | A47K 11/06 4/452 |
| 7,856,676 B2 * | 12/2010 | Akagi | A61B 1/04 210/238 |
| 2001/0034904 A1 * | 11/2001 | Phillips | A47K 11/06 4/484 |
| 2003/0221249 A1 * | 12/2003 | Shirkey | A47K 11/06 4/484 |
| 2010/0175179 A1 * | 7/2010 | Hills | A47K 11/06 4/484 |

* cited by examiner

*Primary Examiner* — J C Jacyna
(74) *Attorney, Agent, or Firm* — Myers Wolin, LLC

(57) ABSTRACT

A portable toilet including: a bowl made of soft material; and a resilient loop integrated with the bowl, the resilient loop forming a rim of the bowl; wherein the bowl comprises a chamber at the bottom of the bowl. The chamber holds a bag which is taken out to cover the bowl during use.

11 Claims, 6 Drawing Sheets

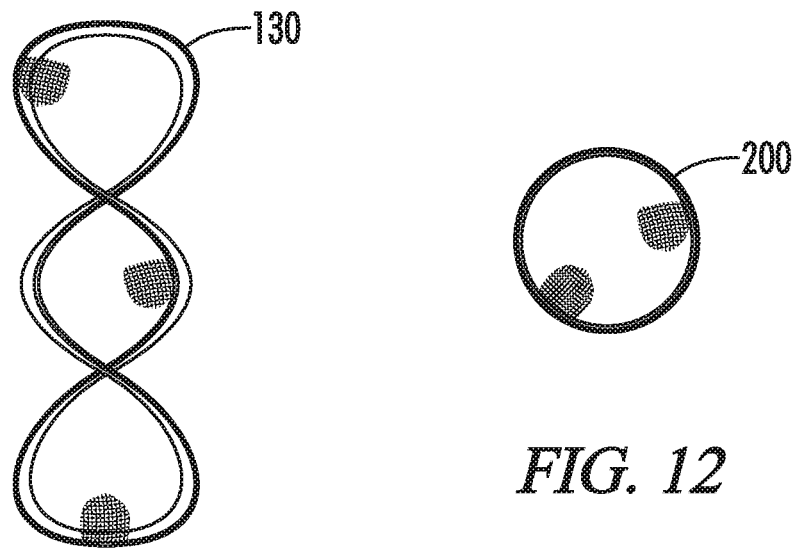
FIG. 11
FIG. 12
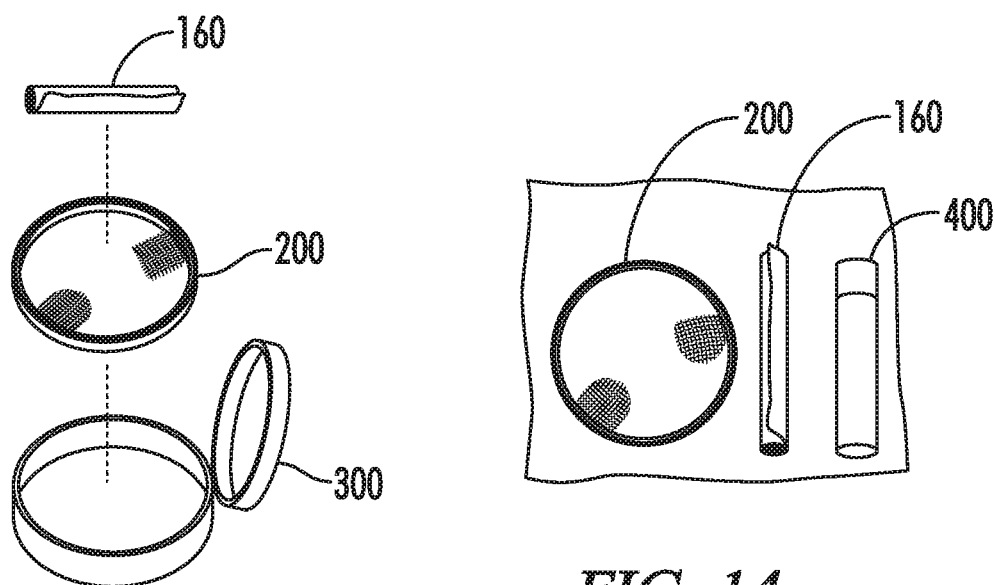
FIG. 13
FIG. 14

PORTABLE TOILET

CROSS REFERENCE TO RELATED APPLICATIONS

This application claims the benefit of U.S. Provisional Patent Application No. 62/559,018 filed on Sep. 15, 2017. The contents of U.S. Provisional Patent Application 62/559,018 are hereby incorporated by reference.

FIELD OF THE INVENTION

This invention relates generally to toilets, and more particularly to portable toilets.

BACKGROUND

In many places, there are no public toilets available. When people need to use the toilet, they have to travel far and look around for facilities. Not having immediate access to the toilet causes inconvenience and discomfort to the people. People may use a bottle when no toilet is available. However, using a bottle is difficult for females due to the problem of spraying. Therefore, there is a need for a portable toilet that accommodates both male and female users, and is also compact, convenient to use, clean and hygienic.

SUMMARY

An embodiment of the present invention provides a portable toilet including: a bowl made of soft material; a resilient loop integrated with the bowl, the resilient loop forming a rim of the bowl; and a chamber attached to the bowl.

BRIEF DESCRIPTION OF THE DRAWINGS

FIG. 11 shows the twisting of the resilient loop of a portable toilet according to an embodiment of the present invention.

FIG. 12 shows the fully twisted resilient loop of a portable toilet according to an embodiment of the present invention.

FIG. 13 shows the bags and the fully twisted and folded portable toilet being stored in a container according to an embodiment of the present invention.

FIG. 14 shows a fully twisted and folded portable toilet with bags and a spray kit according to an embodiment of the present invention.

DETAILED DESCRIPTION OF THE PREFERRED EMBODIMENTS

Figure 1:
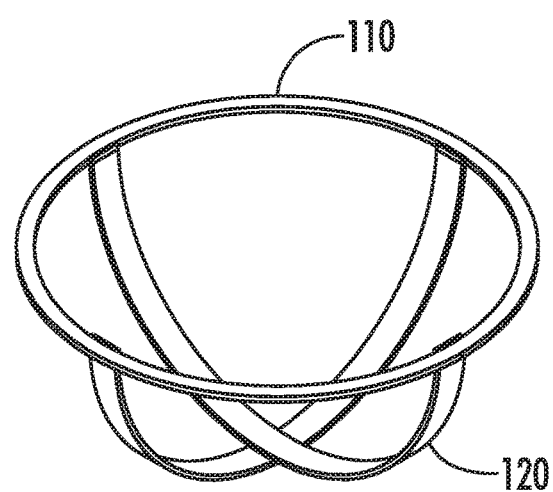
FIG. 1 shows a frame for support a portable toilet according to an embodiment of the present invention.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Figure 8:
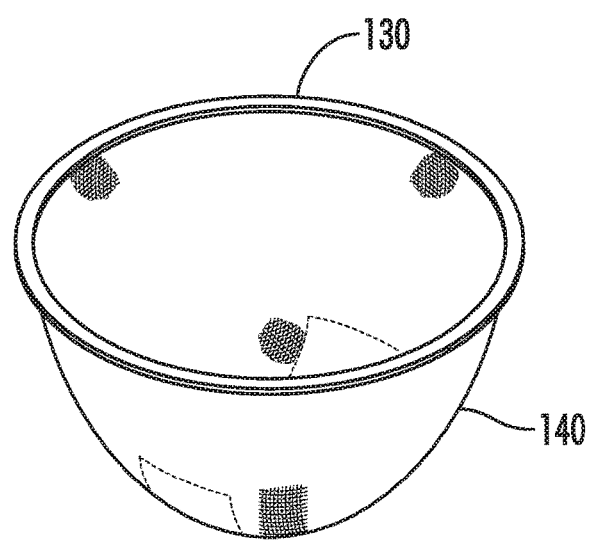
FIG. 8 shows a portable toilet being used alone according to an embodiment of the present invention.

An embodiment of a portable toilet is shown in FIG. 8. The portable toilet includes a bowl 140, made of a soft material, such as cloth or fabric, plastic, netting, leather, paper, rubber, etc., so that the bowl is collapsible and can be folded. Integrated with the bowl is a rim 130. The rim is made of a resilient material, such as steel, plastic, fiber glass, etc., so that it allows the toilet to be folded into a smaller package and allows the toilet to spring back to its original bowl shape when unfolded. In one embodiment, the bowl is configured to have a channel in the soft material around the circumference for insertion and integration of the resilient material. Other means of integrating the resilient material into the bowl, such as threads, glue, rivets, zippers, etc., are also contemplated.

Figure 3:
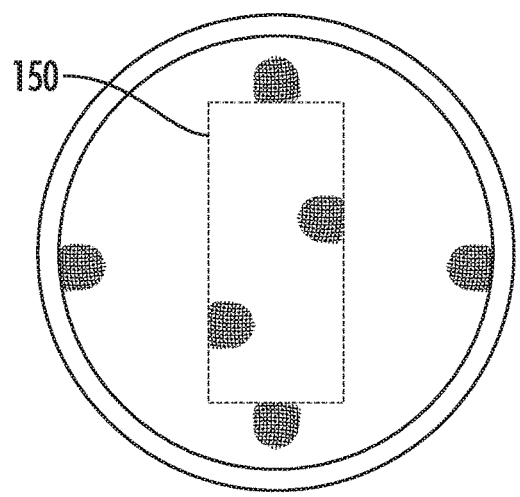
FIG. 3 shows the top view of a portable toilet according to an embodiment of the present invention.
Figure 4:
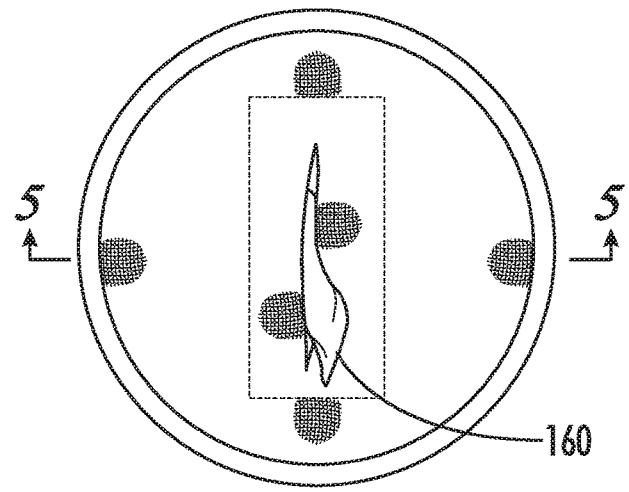
FIG. 4 shows the top view of a portable toilet with bags in the bottom according to an embodiment of the present invention.
Figure 5:
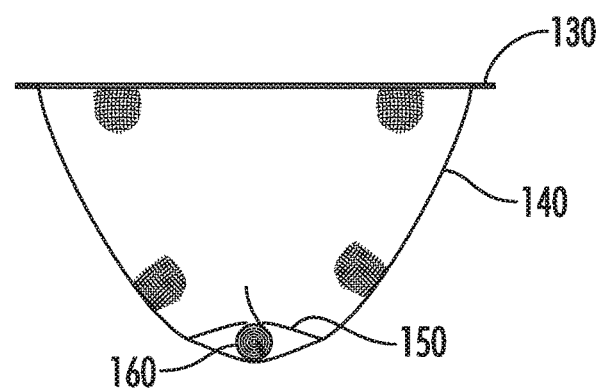
FIG. 5 shows the cross-sectional view of the portable toilet with bags in the bottom according to an embodiment of the present invention.
Figure 9:
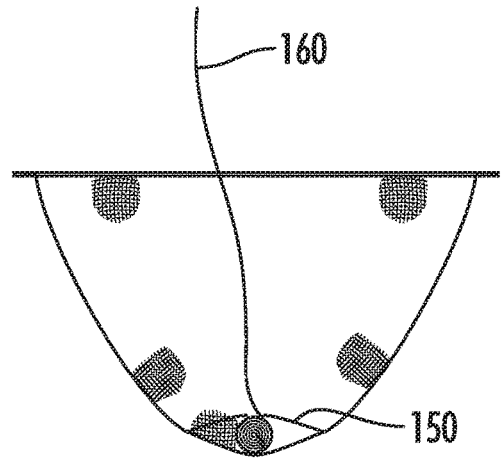
FIG. 9 shows the cross-sectional view of a bag being pulled out from the chamber of a portable toilet according to an embodiment of the present invention.
Figure 10:
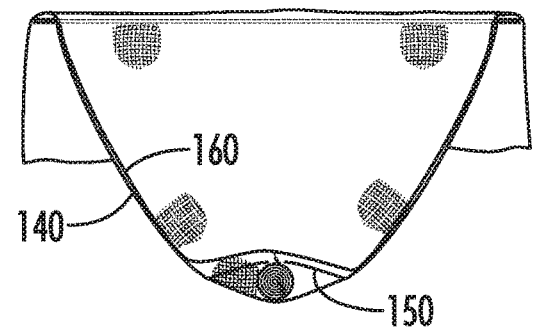
FIG. 10 shows the cross-sectional view of a bag stored in the chamber of a portable toilet according to an embodiment of the present invention.

FIG. 3 is a top view of the portable toilet where a chamber 150 is located at the bottom of the bowl. Note that the chamber can be located elsewhere inside the bowl. The chamber may be permanently attached to the bowl, or it can be removable and attached to the bowl with a fastener, such as VELCRO, button, adhesive, etc. The chamber is used for storing bags 160 as shown in the top view in FIG. 4 and the cross-sectional view in FIG. 5. One or more bags are rolled or folded to fit into the chamber 150. The chamber has an opening to allow the dispensing of the bag, and the bag extends outward to allow for gripping. The opening can be vertical or horizontal. In one embodiment, the bags can be dispensed from continuous roll. FIG. 9 shows the cross-sectional view of a bag 160 being pulled out from the chamber 150. Once the bag is pulled out, it can be used to cover the inside of the bowl. The bag can be discarded after use so that the bowl stays clean. FIG. 10 is a cross-sectional view of the portable toilet with a bag in place. As can be seen from FIG. 10, the bag 160 is placed on top of the inner surface of the bowl 140 and the chamber 150.

Figure 2:
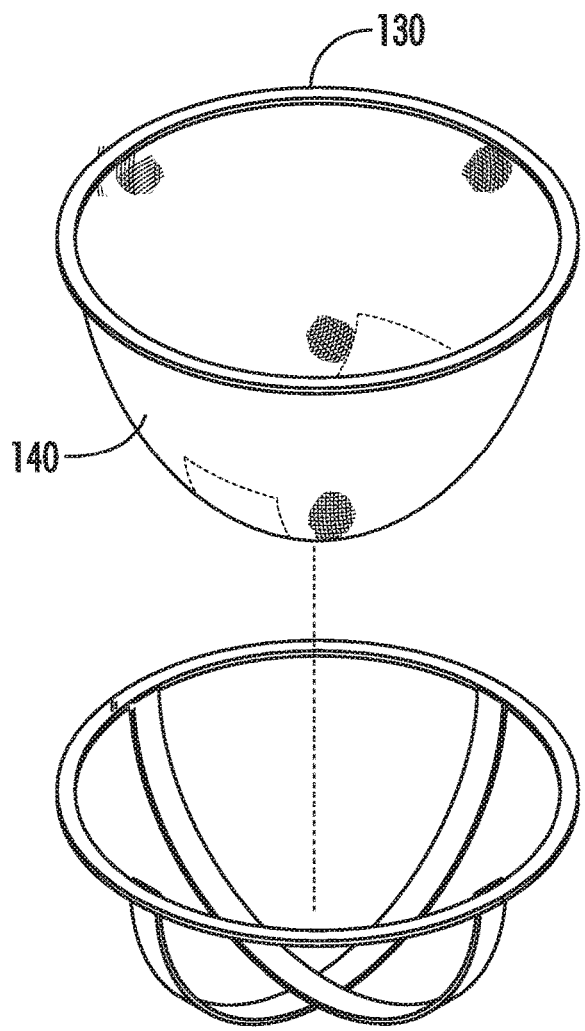
FIG. 2 shows a portable toilet being fitted into the frame according to an embodiment of the present invention.
Figure 6:
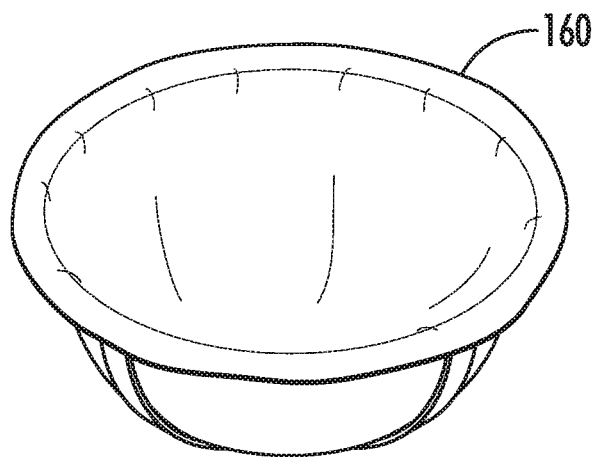
FIG. 6 shows a bag in place on a portable toilet according to an embodiment of the present invention.

In another embodiment of the invention, an optional frame can be used to provide some rigidity to the portable toilet. FIG. 1 shows the frame with a rim 110 and one or more support bars 120. FIG. 2 shows that the bowl 140 is fitted into the frame so that the frame help to retain the bowl shape of the portable toilet. FIG. 6 shows the bag 160 being put in place over the bowl fitted into the frame.

Figure 7:
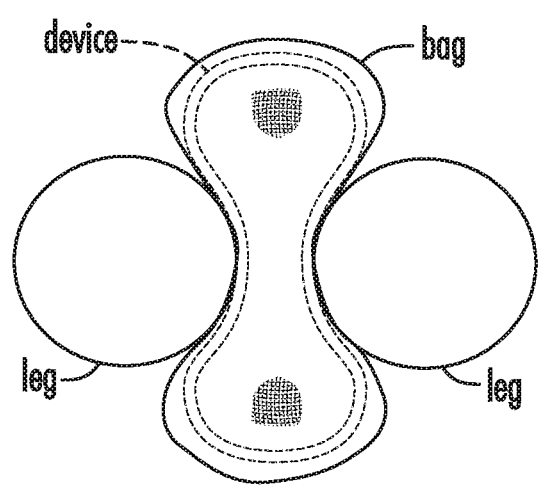
FIG. 7 illustrates the top view of a person using a portable toilet according to an embodiment of the present invention.
Figure 15:
FIG. 15 illustrate a portable toilet in use according to an embodiment of the present invention.

To use the portable toilet, a bag is pulled out from the chamber and put in place to cover the bowl. The user put the toilet between the legs as shown in FIG. 15. Because the rim is made of a resilient material, the rim can be deformed into a dumbbell shape or peanut shell shape when squeezed by the inner thighs as shown in FIG. 7. In one embodiment, the shape of the chamber 150 elongated, such that the length of chamber 150 is aligned with the dumbbell shape when squeezed. This would minimize the stress to the bags in the chamber, and provide a natural direction for user to properly align the toilet when placing the toilet between the thighs. FIG. 15 also illustrates that the user holds the two ends of the dumbbell-shaped rim with one hand in front and one hand behind of the body. In one embodiment, the portable toilet includes handles attached to opposite sides of the rim for extra support.

In order to make the toilet easier to carry and store, the toilet can be twisted to form multiple loops of smaller diameter as shown in FIG. 11. The smaller loops and be folded and stacked together in a fully twisted form 200 as shown in FIG. 12. An optional container 300 can be used to store the fully twisted toilet 200 and a roll of bags 160 as shown in FIG. 13. In another embodiment, the toilet can be packaged as a kit including a fully twisted toilet 200, a roll of bags 160 and a sanitizing spray 400.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A portable toilet comprising:
a bowl made of soft material;
a resilient loop integrated with the bowl, the resilient loop forming a rim of the bowl; and
a chamber attached to the bowl,
one or more folded or rolled up bag located in the chamber, and
wherein each of the one or more folded or rolled up bag is configured to cover the inside of the bowl when unfolded, and
wherein, when covering the inside of the bowl, the bag is a liner that insulates a fluid receiving interior of the liner from the chamber attached to the bowl.

2. The portable toilet of claim 1, wherein the resilient loop is configured to be twisted to form multiple stackable loops, such that the portable toilet can be collapsed and folded.

3. The portable toilet of claim 1, further comprising a frame comprising a support rim and one or more support beams, wherein the bowl is configured to fit into the frame.

4. The portable toilet of claim 2, further comprising a container configured to hold the portable toilet in folded form.

5. The portable toilet of claim 1, wherein the soft material is netting fabric.

6. The portable toilet of claim 1, wherein the rim is configured to form a dumbbell shape when force is applied toward the center at opposite locations of the rim.

7. The portable toilet of claim 1, wherein the chamber is located at the bottom of the bowl.

8. The portable toilet of claim 1, wherein the resilient material is located inside a channel around the circumference of the bowl.

9. A method of using a portable toilet comprising a bowl made of soft material, a resilient loop integrated with the bowl, the resilient loop forming a rim of the bowl, and a chamber attached to the bowl, the method comprising:
pulling out a bag stored in the chamber;
covering the inside surface of the bowl with the bag;
placing the toilet between the thighs of the user;
squeezing the rim with the thighs such that the toilet is deformed into a dumbbell shape; and
discarding the bag after use.

10. The method of claim 9, wherein the resilient loop of the toilet has been twisted to form multiple loops stacked together, the method further comprising:
untwisiting the resilient loop before use; and
retwisting the resilient loop back to its twisted form after use.

11. A portable toilet kit, comprising:
a portable toilet;
a roll of bags; and
a sanitizing spray;
wherein the portable toilet comprises:
a bowl made of soft material;
a resilient loop integrated with the bowl, the resilient loop forming a rim of the bowl; and
a chamber attached to the bowl,
one or more folded or rolled up bag located in the chamber, and wherein each of the one or more folded or rolled up bag is configured to cover the inside of the bowl when unfolded, and wherein, when covering the inside of the bowl, the bag is a liner that insulates a fluid receiving interior of the liner from the chamber attached to the bowl.

* * * * *